(12) United States Patent
Livoreil et al.

(10) Patent No.: US 6,372,235 B1
(45) Date of Patent: Apr. 16, 2002

(54) COMPOSITIONS IN SOLID FORM COMPRISING AN OIL AND A SPECIFIC GELLING COMPOUND, COSMETIC TREATMENT PROCESSES, AND USE OF THE COMPOUND

(75) Inventors: Aude Livoreil, Aulnay sous Bois Cedex; Nathalie Mougin, Paris, both of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/617,131

(22) Filed: Jul. 14, 2000

(30) Foreign Application Priority Data

Jul. 15, 1999 (FR) .............................. 99 09178

(51) Int. Cl.$^7$ ................................. A61K 7/00
(52) U.S. Cl. ...................... 424/401; 424/70.1
(58) Field of Search ................. 424/401, 70.1

(56) References Cited

FOREIGN PATENT DOCUMENTS

EP      0 291 334      11/1988

OTHER PUBLICATIONS

Patent Abstracts of Japan, vol. 1998, No.13, Nov. 30, 1998 (JP 10 212213).*

Patent Abstracts of Japan, vol. 1988, No. 13, Nov. 30, 1998 (JP 10 212213).

* cited by examiner

Primary Examiner—Jose' G. Dees
Assistant Examiner—Konata M. George
(74) Attorney, Agent, or Firm—Finnegan, Henderson, Farabow, Garrett & Dunner, L.L.P.

(57) ABSTRACT

Compositions, for example cosmetic or dermatological compositions, which are in solid form, and which comprise at least one oil, at least one compound of formula I, and less than about 5% by weight of wax relative to the total weight of the composition. The compositions can be in the form of a translucent or even transparent anhydrous stick. They can be, for example, optionally colored "transfer-resistant" or "non-migrating" compositions. Cosmetic treatment processes for a support chosen from facial and body skin, mucous membranes and keratin fibers, comprising applying these compositions to the support.

60 Claims, No Drawings

COMPOSITIONS IN SOLID FORM COMPRISING AN OIL AND A SPECIFIC GELLING COMPOUND, COSMETIC TREATMENT PROCESSES, AND USE OF THE COMPOUND

The present invention relates to a solid composition, for example a cosmetic composition such as a care, treatment and/or make-up composition for the skin, including the scalp, and/or for the lips of human beings, comprising a thickened liquid fatty phase. The composition can be in the form of a stick or tube of make-up, such as a lipstick, the application of which can give a glossy, non-migrating deposit.

It is common practice to use a structured, i.e., thickened or gelled, liquid fatty phase in compositions, such as in cosmetic and dermatological compositions, in order to obtain the desired consistency. The thickening of oils (or of phases that are liquid at room temperature) makes it easier to take up the product from its packaging without any significant loss, to limit the diffusion of the product to the local treatment area, to distribute the product uniformly over the local treatment area, or to be able to use the product in amounts that are sufficient to obtain the desired cosmetic or dermatological effect. This is especially the case in solid compositions such as deodorants, lip balms and lipsticks, concealer products and cast foundations. This thickening is desirable for care, hygiene or make-up compositions such as lipsticks, which are preferably distributed homogeneously over the local surface to be treated, as well as for hair compositions, which are preferably spread and distributed uniformly along the keratin fibers and which preferably do not run down the forehead, the nape of the neck, the face or into the eyes.

To overcome these problems, use is usually made of waxes or fillers. Unfortunately, these waxes and/or fillers have a tendency to make the composition matte and opaque, which is not always desirable, in particular for a lipstick. Specifically, women are always in search of a lipstick in the form of a tube which gives a glossy film; moreover, certain compositions such as lip balms or ointments can be in the form of translucent, or even transparent, sticks.

It is also known practice to thicken oils with polymeric thickeners. Unfortunately, the known thickeners for oils have to be used in large amounts in order to obtain a gel of high viscosity, for example of greater than 1.3 Pa.s. However, too large an amount of thickener can give the composition inadequate cosmetic properties, in particular, a sticky feel and a lack of slipperiness. These drawbacks can potentially be very inconvenient, or even prohibitive.

The structuring of the liquid fatty phase makes it possible to limit its exudation from solid compositions and, in addition, to limit the migration of this phase in wrinkles and fine lines after it has been deposited on the skin or the lips, which is a particularly desired quality for a lipstick. The reason for this is that a large migration of the liquid fatty phase, charged with dyestuffs, leads to an unaesthetic effect around the lips, which particularly accentuates wrinkles and fine lines. This migration is often mentioned by women as a major defect of conventional lipsticks.

The aim of the present invention is to produce a composition, such as a cosmetic composition, which is in solid form, comprises little or no wax, and is capable of conserving good cosmetic properties, such as a certain level of translucency.

A subject of the invention is thus a composition, such as a cosmetic or dermatological composition, which is in solid form, comprising at least one oil and at least one compound defined by formula I as described below, wherein the composition comprises less than about 5% by weight of wax relative to the total weight of the composition.

The composition can be in the form of a translucent, or even transparent, anhydrous stick. It can also be an optionally colored "transfer-resistant" or "non-migrating" composition.

Another subject of the invention is a cosmetic treatment process for a support chosen from facial and body skin, mucous membranes and keratin fibers, comprising applying to the support a composition as defined above.

Another subject of the invention is the use in a composition, such as a cosmetic or dermatological composition, which is in solid form and which comprises at least one oil and less than about 5% of wax relative to the total weight of the composition, of a sufficient amount of at least one compound of formula I described below, in order to structure/gel the composition.

It has been found that the use of the compounds of formula I makes it possible to structure liquid fatty phases, or oily phases, or even to gel them completely, and thus to obtain stable cosmetic compositions in solid gelled form, which may be free of waxes. This is true even when a very low content of the compound of formula I is used.

The composition according to the invention has good cosmetic properties: it is not sticky when applied, and is slippery and easy to apply. It gives a homogeneous, uniform film which covers well and is comfortable to wear.

Furthermore, the composition can advantageously be clear, transparent or translucent. The terms "translucent" and "transparent" can be understood by the conventional definitions given in the dictionary. Thus, a translucent composition allows light to pass through without, however, allowing the contours of objects to be sharply distinguished. A transparent composition allows light to pass through easily and allows objects to be sharply distinguished through its thickness.

In general, a transparent composition will have a maximum light transmittance value, irrespective of the wavelength from 400 nm to 800 nm, of at least 35% through a 1 cm thick sample, and in another embodiment, of at least 50% (see EP 291 334, the disclosure of which is incorporated by reference herein). A translucent composition, for its part, will generally have a maximum light transmittance value ranging from 2% to 35%.

The transmittance can be measured by placing a 1 cm thick sample in the light beam of a spectrophotometer working in the wavelengths of the luminous spectrum.

Moreover, the compounds of formula I can advantageously be used to prepare colored "transfer-resistant" compositions, for which there is very limited migration of the colored film in wrinkles and fine lines, such as those around the lips or the eyes. These compositions also have the advantage of not being deposited, or of being only slightly deposited, on certain supports with which they are placed in contact, such as, for example, a glass, an item of clothing or the skin.

The composition according to the invention thus comprises at least one compound corresponding to formula I:

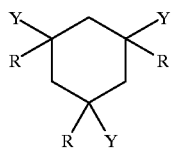

wherein:
the variables R are chosen, independently of each other, from a hydrogen atom and a linear or branched, saturated hydrocarbon-based chain comprising 1 to 6 carbon atoms, and in another embodiment, 1 to 4 carbon atoms; and the variables Y are chosen, independently of each other, from the following groups: —CO—S—R'; —CO—NHR'; NH—COR' and —S—COR'; wherein the variables R' are chosen, independently of each other, from:
a hydrogen atom;
an aryl group;
an aralkyl group, such as an aryl group substituted with a linear or branched, saturated hydrocarbon-based chain comprising 1 to 22 carbon atoms, and in another embodiment, 10 to 18 carbon atoms; and
a linear, branched or cyclic, saturated hydrocarbon-based chain comprising 1 to 22 carbon atoms, and in another embodiment, 10 to 18 carbon atoms, and optionally substituted with one or more groups chosen from aryl, ester, amide and urethane groups; and/or optionally comprising one or more hetero atoms chosen from O, S and N; and/or optionally substituted with one or more fluorine atoms and/or hydroxyl radicals.

In one embodiment of the invention, the variables R are hydrogen atoms.

In another embodiment, the variables Y are chosen, independently from each other, from the groups —CO—NHR' and —NH—COR'.

According to another embodiment of the invention, the variables R' are chosen, independently from each other, from an aryl group, an aralkyl group wherein the linear or branched alkyl chain comprises 12 to 16 carbon atoms, and a linear or branched $C_{12}$–$C_{18}$ alkyl chain.

Among the representative compounds of formula I, mention may be made, for example, of the compounds wherein Y is a group —CO—NHR', wherein R' is chosen from an aryl group substituted with a linear or branched $C_{12}$–$C_{16}$ alkyl chain, and an unsubstituted, linear or branched $C_{12}$–$C_{18}$ alkyl chain.

The three substituents represented by Y can be, in the compound of formula I, in cis-cis, cis-trans or trans-trans conformation relative to each other. According to one embodiment, at least one of these substituents can be placed in an equatorial position on the cyclohexane ring, and in another embodiment, all the substituents Y are placed in an equatorial position.

Among the compounds which may be used in the context of the invention, mention may be made of:

cis-1,3,5-tris(dodecylaminocarbonyl)cyclohexane,
cis-1,3,5-tris(octadecylaminocarbonyl)cyclohexane,
cis-1,3,5-tris[N-(3,7-dimethyloctyl)aminocarbonyl] cyclohexane,
trans-1,3,5-trimethyl-1,3,5-tris(dodecylaminocarbonyl) cyclohexane, and
trans-1,3,5-trimethyl-1,3,5-tris(octadecylaminocarbonyl) cyclohexane.

The compounds of formula I are well known to those skilled in the art and can be prepared according to the usual processes.

The compounds of formula I can be present in the composition in an amount which can readily be determined by a person skilled in the art as a function of the desired effect, for example in an amount ranging from 1 to 40% by weight, or 2 to 10% by weight, relative to the total weight of the composition. In some embodiments, the compounds of formula I are present in an amount ranging from 3 to 8% by weight or even 4 to 6% by weight, relative to the total weight of the composition.

It has moreover been observed that even the use of a small amount of compounds of formula I, for example about 2 to 6% by weight, can lead to an adequate gelation of the composition according to the invention. This is due to the large thickening power of the compounds of formula I, which enables them to be effective at low concentration, for example of about 2 to 6% by weight, whereas it would be necessary to use 10 to 20% by weight of common gelling agents in order to obtain an equivalent result.

Without being bound by the present explanation, it has been observed that the structuring, or gelation, of oils by means of the compounds of formula I may be due to the formation of piles in the form of columns of the molecules of compounds of formula I, resulting in the formation of a network of fibers or lamellae, comprising the compounds of formula I and the oils. This network of fibers or lamellae does not scatter light, resulting in a certain level of translucency, or even transparency.

The composition according to the invention can further comprise at least one cosmetically or dermatologically acceptable oil which is liquid at room temperature (25° C.). These oils can be hydrocarbon-based and/or silicone and/or fluoro oils. They can be of animal, plant, mineral or synthetic origin.

Representative oils which can be mentioned include:
hydrocarbon-based oils of animal origin such as perhydrosqualene;

hydrocarbon-based plant oils such as liquid triglycerides of fatty acids of 4 to 10 carbon atoms, such as heptanoic or octanoic acid triglycerides; sunflower oil; corn oil; soybean oil; marrow oil; grapeseed oil; groundnut oil; sweet almond oil; beauty-leaf oil; palm oil; sesame oil; hazelnut oil; apricot oil; macadamia oil; castor oil; avocado oil; caprylic/capric acid triglycerides such as those sold by the company Stearineries Dubois or those sold under the names Miglyol 810, 812 and 818 by the company Dynamit Nobel; jojoba oil; and karite butter;

linear or branched hydrocarbons of mineral or synthetic origin, such as liquid paraffins and derivatives thereof, petroleum jelly, polydecenes, purcellin oil, and hydrogenated polyisobutene such as parleam;

synthetic esters and ethers, in particular of fatty acids, such as the oils of formula $R_3COOR_4$, wherein $R_3$ is a higher fatty acid residue comprising 7 to 29 carbon atoms, and $R_4$ is a hydrocarbon-based chain comprising 3 to 30 carbon atoms, such as, for example, purcellin oil, isopropyl myristate, 2-ethylhexyl palmitate, 2-octyldodecyl stearate, 2-octyldodecyl erucate, and isostearyl isostearate; hydroxylated esters such as isostearyl lactate, octyl hydroxystearate, octyldodecyl hydroxystearate, diisostearyl malate, triisocetyl citrate, and fatty alkyl heptanoates, octanoates and decanoates; polyol esters such as propylene glycol dioctanoate, neopentyl glycol diheptanoate and diethylene glycol diisononanoate; and pentaerythritol esters;

fatty alcohols comprising 12 to 26 carbon atoms, such as octyldodecanol, 2-butyloctanol, 2-hexyldecanol, 2-undecylpentadecanol and oleyl alcohol;

partially hydrocarbon-based and/or silicone-containing fluoro oils;

silicone oils such as volatile or non-volatile, linear or cyclic polydimethylsiloxanes (PDMSs); alkyldimethicones; silicones modified with aliphatic and/or aromatic groups, which are optionally fluorinated, or with functional groups such as hydroxyl, thiol and/or amine groups; phenylsilicone oils such as polyphenylmethylsiloxanes or phenyltrimethicones; and mixtures thereof.

The oils used can be volatile and/or non-volatile. The term "volatile oil" means an oil which is capable of evaporating at room temperature from a support onto which it has been applied. In other words, it is an oil which has a measurable vapor pressure at 25° C. and 1 atmosphere, such as a vapor pressure greater than 0 Pa, and ranging, for example, from $10^{-3}$ mmHg to 300 mmHg (0.13 Pa to 40,000 Pa).

Mention can be made, for example, of volatile silicone oils, such as volatile cyclic or linear silicones, and cyclocopolymers. Mention may also be made of volatile hydrocarbon-based oils, such as volatile isoparaffins and volatile fluoro oils.

In one specific embodiment, the volatile oils can constitute the majority of the oily phase. Thus, they can be present therein in a proportion of at least 50% by weight, and in some embodiments, in a proportion of at least 75% by weight, or even 100% by weight, of the oily phase.

The oils can be present in the composition in a proportion ranging from 5% to 99% by weight relative to the total weight of the composition, and in one embodiment, from 20% to 75% by weight.

The composition according to the invention can be in solid form. This means that, in the absence of mechanical or thermal stimulation (such as heating), no collapse of the composition is observed when it is outside the container containing it.

The composition can have the conventional viscoelastic behavior of a composition of solid type.

Moreover, the hardness of the composition according to the invention can be such that the composition is self-supporting and can disintegrate readily to form a satisfactory deposit on the skin and the lips. This hardness can range from 0.04 N to 3 N, in some embodiments, from 0.1 N to 2.5 N, and in other embodiments, from 0.5 N to 2 N. This hardness can be measured according to a method of penetration of a probe into the composition and in particular using a texture analyser (for example TA-XT2 from Rheo) equipped with an acrylic cone with an apex angle of 45°. The hardness measurement is carried out at 22° C. at the center of five samples of the composition, according to the method described in the examples.

The composition can comprise little or no wax. This means that the composition comprises less than about 5% by weight of wax, relative to the total weight of the composition, and in other embodiments, less than 2% by weight, or even less than 0.5% by weight of wax. The composition can contain no waxes (i.e., 0%).

For the purposes of the present invention, a wax is a lipophilic fatty compound, which is solid at room temperature (about 25° C.), which undergoes a reversible solid/liquid change of state, which has a melting point of greater than about 40° C. which may range up to 200° C., and which has an anisotropic crystal organization in the solid state.

In general, the size of the crystals in the wax is such that the crystals defract and/or scatter light, giving the composition containing them a more or less opaque, cloudy appearance. By bringing the wax to its melting point, it is possible to make it miscible with oils and to form a microscopically homogeneous mixture, but by returning the temperature of the mixture to room temperature, a microscopically and macroscopically detectable recrystallization of the wax in the oils of the mixture is obtained (opalescence).

For the purposes of the invention, the waxes are those generally used in cosmetics and dermatology.

Representative waxes that may be mentioned include natural waxes of animal, plant or mineral origin, such as beeswax, montan wax, carnauba wax, candelilla wax, china wax, flax wax, pine wax, cotton wax, ouricury wax, lignite wax, rice bran wax, sugar cane wax, Japan wax and cork fiber wax.

Mention may also be made of paraffin waxes, microcrystalline waxes, lanolin wax, ozokerites, hydrogenated oils with a melting point of greater than about 40° C., such as hydrogenated jojoba oil, polyethylene waxes derived from the polymerization of ethylene, waxes obtained by Fischer-Tropsch synthesis, fatty acid esters and glycerides with a melting point of greater than about 40° C., and silicone waxes such as alkyl, alkoxy and/or esters of poly(di) methylsiloxane that are solid at 40° C.

The composition according to the invention can moreover comprise the constituents usually used in the type of application envisaged.

For example, it can comprise one or more organic solvents chosen from:

ketones that are liquid at room temperature, such as methyl ethyl ketone, methyl isobutyl ketone, diisobutyl ketone, isophorone, cyclohexanone and acetone;

alcohols that are liquid at room temperature, such as ethanol, isopropanol, diacetone alcohol, 2-butoxyethanol and cyclohexanol;

glycols that are liquid at room temperature, such as ethylene glycol, propylene glycol and pentylene glycol;

propylene glycol ethers that are liquid at room temperature, such as propylene glycol monomethyl ether, propylene glycol monomethyl ether acetate and dipropylene glycol mono-n-butyl ether;

short-chain esters (comprising 3 to 8 carbon atoms in total) such as ethyl acetate, methyl acetate, propyl acetate, n-butyl acetate and isopentyl acetate;

ethers that are liquid at room temperature, such as diethyl ether, dimethyl ether and dichlorodiethyl ether;

alkanes that are liquid at room temperature, such as decane, heptane, dodecane and cyclohexane;

cyclic aromatic compounds that are liquid at room temperature, such as toluene and xylene; and aldehydes that are liquid at room temperature, such as benzaldehyde and acetaldehyde.

It is also possible to incorporate a hydrophilic phase into the composition according to the invention, for example in an amount ranging from 0 to 10% by weight relative to the total weight of the composition, and in some embodiments, from 1 to 5% by weight. This lipophilic phase can comprise hydrophilic active agents and/or hydrophilic gelling agents. For example, it can comprise moisturizers such as glycerol.

The composition can also comprise a dyestuff which can be chosen from lipophilic dyes, hydrophilic dyes, pigments and nacres usually used in cosmetic or dermatological compositions, and mixtures thereof. This dyestuff is generally present in a proportion ranging from 0.01% to 40% relative to the total weight of the composition, and in some embodiments, from 5% to 25% by weight.

Thus, the composition can comprise a particulate phase, which is generally present in a proportion ranging from 0 to 30% by weight, and in some embodiments, from 0 to 20% by weight, and which can comprise pigments and/or nacres and/or fillers usually used in cosmetic compositions. The term "pigments" should be understood as meaning white or colored, mineral or organic particles intended to color and/or opacify the composition. The term "fillers" should be understood as meaning colorless or white, mineral or synthetic, lamellar or non-lamellar particles intended to give body or rigidity to the composition, and/or softness, a matte effect and/or uniformity to the make-up result. The term "nacres" should be understood as meaning iridescent particles which reflect light.

The pigments can be white or colored, mineral and/or organic, of micrometric or nanometric size. Mineral pigments which may be mentioned include titanium dioxide, zirconium dioxide and cerium dioxide, as well as zinc oxide, iron oxide, chromium oxide and ferric blue. Organic pigments which may be mentioned include carbon black and barium, strontium, calcium and aluminium lakes.

Among the nacres which may be envisaged, mention may be made of mica coated with titanium oxide, with iron oxide, with natural pigment and with bismuth oxychloride, as well as colored titanium mica.

The fillers can be mineral or synthetic, and lamellar or non-lamellar. Mention may be made of talc, mica, silica, kaolin, Nylon powder, polyethylene powder, Teflon, starch, titanium mica, natural mother-of-pearl, boron nitride, microspheres such as Expancel (Nobel Industrie), Polytrap (Dow Corning) and silicone resin microbeads (Tospearls from Toshiba, for example).

The composition according to the invention can also comprise any additive usually used in the field under consideration, for example in cosmetics, such as antioxidants, fragrances, dyes, essential oils, preserving agents, cosmetic active agents, vitamins, essential fatty acids, sphingolipids, self-tanning compounds such as DHA, sunscreens, surfactants, gelling agents, polymers, for example hydrocarbon-based polymers such as polybutene, polyalkylenes, polyacrylates, and silicone polymers or derivatives which are compatible with fatty substances. These additives can generally be present in the composition in a proportion ranging from 0 to 10% by weight.

Needless to say, a person skilled in the art will take care to select this or these optional additional compound(s), and/or the amount thereof, such that the advantageous properties of the composition according to the invention are not, or are not substantially, adversely affected by the addition envisaged.

The compositions according to the invention can be applied to facial and body skin, to mucuous membranes and/or to keratin fibers such as the nails, the eyelashes and the hair.

They can be in any envisageable pharmaceutical form, such as a solid or soft oily gel optionally comprising water; a solid or gelled oil-in-water, water-in-oil or multiple emulsion; a dispersion of oil in water; and a multiphase system, such as a two-phase system. They can have the appearance of a cream, an ointment, a soft paste, a salve, or a cast or molded solid, such as a stick.

They can be, for example, in the form of a stick or a dish, in the form of a transparent anhydrous rigid gel, or in the form of a transparent anhydrous stick.

The gelation of the oil is such that a rigid structure in the form of a tube or a stick can be obtained. When they are colored, these tubes can give, after application, a deposit of homogeneous color which does not migrate in the wrinkles and fine lines of the skin, such as those surrounding the lips, or those around the eyes.

These compositions can find an application as body hygiene compositions, for example in the form of deodorant sticks; as hair compositions, for example as styling sticks or make-up sticks for the hair; as make-up compositions for facial or body skin or for mucous membranes, for example as lipsticks, foundations cast as a stick or a dish, face powders, eyeshadows, fixing bases to be applied to a conventional lipstick, concealer sticks, lip glosses, eyeliners, mascaras or temporary tattoo products; as care compositions for the skin or mucous membranes, for example as lipcare balms or bases, body ointments or daily care creams; and as antisun compositions or self-tanning compositions.

For example, the compositions can find an application as transfer-resistant make-up or care compositions, such as transfer-resistant lipsticks or transfer-resistant foundations.

The invention is illustrated in greater detail in the non-limiting examples which follow.

EXAMPLE 1

The compound used in this example corresponds to formula I in which each R is hydrogen and each Y is —CO—NHR' wherein R' is a linear alkyl chain comprising 18 carbon atoms.

The following were mixed together at room temperature with stirring:

250 mg of this compound, and 5 ml of isododecane, i.e., a mixture containing 5% of the compound of formula I.

The mixture was heated to 120° C. with stirring, until homogenized. It then became to transparent, homogeneous and fluid. The homogeneous mixture was then left to cool slowly to room temperature (25° C.).

A solid, hard composition was thus obtained, which did not collapse when it was outside its container, in the absence of any mechanical or thermal stimulation. This composition could be spread by simple pressure and gave an oily, homogeneous film.

EXAMPLE 2

The following were mixed together at room temperature with stirring:

250 mg of the compound of formula I of Example 1, 5 ml of isododecane, and 25 mg of pigment (iron oxides).

The mixture was heated to 120° C. until homogenized. It became transparent, colored, homogeneous and fluid. The mixture was then left to cool slowly to room temperature.

A solid, colored composition in the form of a stick was thus obtained. This composition showed no separation of the pigment over time. It gave an oily, homogeneous film.

EXAMPLE 3

The compound of formula I used in this example corresponds to formula I in which each R is hydrogen and each Y is —CO—NHR' wherein R' is a linear alkyl chain comprising 12 carbon atoms.

The following were mixed together at room temperature with stirring:

200 mg of this compound and 5 ml of isododecane, i.e., a mixture containing 4% by weight of the compound of formula I.

The mixture was heated to 120° C. with stirring, until homogenized. It then became transparent, homogeneous and fluid. The homogeneous mixture was then left to cool slowly to room temperature.

A translucent, virtually transparent, solid, hard composition was thus obtained, which did not collapse when it was outside its container, in the absence of any mechanical or thermal stimulation. It could be in the form of a stick. This composition gave an oily, homogeneous film.

A) The hardness of the stick obtained was measured using a TA-XT2 texture analyser (from Rheo), at 22° C., using a smooth acrylic cone with an apex angle of 45° C., and a total height which was greater than the penetration distance. The cone penetrated into the sample to a distance of 5 mm, at a speed of 2 mm/s. It was then kept immobile for 300 s, after which it was removed from the sample at a speed of 2 mm/s. The force exerted by the sample on the measuring body was recorded continuously.

The maximum force was detected at the end of the penetration phase. This force value reflects the hardness of the sample.

In the present case, a hardness of 0.86 N (reproducible) was obtained.

B) The transparency or translucency was measured by measuring the transmittance, i.e., the percentage of light transmitted through a given sample, in the wavelength range corresponding to the visible range, i.e., from 400 nm to 800 nm.

This transmittance was measured continuously through a sample of thickened oil, placed in a glass cuvette with an optical path length of 1 cm, by difference with a so-called reference sample containing the same pure oil.

The measuring instrument was a Perkin-Elmer Lambda UV-Vis spectrophotometer.

The above composition was heated until it was in the form of a homogeneous fluid, and was poured directly into the measuring cuvette. The cuvette was maintained at room temperature until its contents cooled. The cuvette was then placed in the machine, the reference cuvette containing pure isododecane also being placed in the machine.

The transmittance was measured from 400 nm to 800 nm.

It varied in a virtually linear continuous manner, from 7% at 400 nm to 37% at 800 nm (maximum value).

EXAMPLE 4

Comparative Example 1) 200 mg of carnauba wax were mixed with 5 ml of isododecane (mixture at a concentration of 4% by weight), with stirring at room temperature. The mixture was heated at 120° C. with stirring, until homogenized. The homogeneous, fluid mixture was left to cool slowly to room temperature.

During the cooling, the formation of a soft two-phase system with grains of wax in a supernatant oily phase was observed. It was not possible to obtain a solid composition.

2) Similarly, a mixture was prepared comprising 500 mg of carnauba wax with 5 ml of isododecane (mixture at a concentration of 10% by weight). After cooling, a homogeneous stick with a hardness of 1.6 N was obtained. However, this stick was completely opaque.

Its transmittance was measured in a manner similar to that of Example 3; the transmittance was 0 throughout the wavelength range scanned. This corresponded fully to a totally opaque sample.

EXAMPLE 5

In a manner similar to that of the preceding examples, a composition according to the invention was prepared, comprising:

| | |
|---|---|
| compound of Example 3 | 0.8 g |
| pigments (iron oxides) | 0.5 g |
| isododecane | 16 ml |
| parleam oil | 4 ml |

A solid, hard, colored stick was obtained.

A colored film was deposited on a glass plate, using the composition thus prepared. The deposit was left to dry for 20 minutes. The deposit was then dry but remained malleable.

A paper tissue was applied to the deposit and was pressed by hand. No colored trace was observed on the tissue.

Mechanical rubbing of the tissue on the deposit did not result in any transfer of color (possible entrainment of material).

The composition thus prepared clearly showed good transfer-resistance properties.

What is claimed is:

1. A composition comprising at least one oil and at least one compound of formula I below:

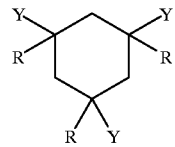

wherein:
the variables R are chosen, independently of each other, from a hydrogen atom and a linear or branched, saturated hydrocarbon-based chain comprising 1 to 6 carbon atoms;
the variables Y are chosen, independently of each other, from the groups —CO—S—R', —CO—NHR', NH—COR' and —S—COR', wherein the variables R' are chosen, independently of each other, from:
a hydrogen atom,
an aryl group,
an aralkyl group, and
a linear, branched, or cyclic, saturated hydrocarbon-based chain comprising 1 to 22 carbon atoms, which is optionally substituted with one or more groups chosen from aryl, ester, amide and urethane groups, and/or optionally comprises one or more hetero atoms chosen from O, S and N, and/or is optionally substituted with one or more fluorine atoms and/or one or more hydroxyl radicals;
wherein said composition is in solid form, and wherein said composition comprises less than about 5% by weight of wax relative to the total weight of the composition.

2. A composition according to claim 1, wherein said composition is a cosmetic or dermatological composition.

3. A composition according to claim 1, wherein said variables R are chosen, independently of each other, from a hydrogen atom and a linear or branched, saturated hydrocarbon-based chain comprising 1 to 4 carbon atoms.

4. A composition according to claim 1, wherein said aralkyl group is an aryl group substituted with a linear or branched, saturated hydrocarbon-based chain comprising 1 to 22 carbon atoms.

5. A composition according to claim 4, wherein said aralkyl group is an aryl group substituted with a linear or branched, saturated hydrocarbon-based chain comprising 10 to 18 carbon atoms.

6. A composition according to claim 1, wherein said variables R' are chosen, independently of each other, from:
a hydrogen atom,
an aryl group,
an aralkyl group, and
a linear, branched, or cyclic, saturated hydrocarbon-based chain comprising 10 to 18 carbon atoms, which is optionally substituted with one or more groups chosen from aryl, ester, amide and urethane groups, and/or optionally comprises one or more hetero atoms chosen from O, S and N, and/or is optionally substituted with one or more fluorine atoms and/or one or more hydroxyl radicals.

7. A composition according to claim 1, wherein:
the variables R are hydrogen atoms; and/or
the variables Y are chosen, independently of each other, from —CO—NHR' and —NH—COR'; and/or
the variables R' are chosen from an aryl group, an aralkyl group wherein the linear or branched alkyl chain comprises 12–16 carbon atoms, and a linear or branched $C_{12}$–$C_{18}$ alkyl chain.

8. A composition according to claim 1, wherein:
the variables R are hydrogen atoms; and
the variables Y are —CO—NHR', wherein R' is chosen from an aryl group substituted with a linear or branched $C_{12}$–$C_{16}$ alkyl chain, and an unsubstituted, linear or branched $C_{12}$–$C_{18}$ alkyl chain.

9. A composition according to claim 1, wherein said at least one compound of formula I is chosen from:

cis-1,3,5-tris(dodecylaminocarbonyl)cyclohexane,
cis-1,3,5-tris(octadecylaminocarbonyl)cyclohexane,
cis-1,3,5-tris[N-(3,7-dimethyloctyl)aminocarbonyl]cyclohexane,
trans-1,3,5-trimethyl-1,3,5-tris(dodecylaminocarbonyl)cyclohexane, and
trans-1,3,5-trimethyl-1,3,5-tris(octadecylaminocarbonyl)cyclohexane.

10. A composition according to claim 1, wherein said at least one compound of formula I is present in an amount ranging from 1 to 40% by weight relative to the total weight of the composition.

11. A composition according to claim 10, wherein said at least one compound of formula I is present in an amount ranging from 2 to 10% by weight relative to the total weight of the composition.

12. A composition according to claim 11, wherein said at least one compound of formula I is present in an amount ranging from 3 to 8% by weight relative to the total weight of the composition.

13. A composition according to claim 12, wherein said at least one compound of formula I is present in an amount ranging from 4 to 6% by weight relative to the total weight of the composition.

14. A composition according to claim 1, wherein said at least one oil is chosen from hydrocarbon-based, silicone, and fluoro oils of animal, plant, mineral, or synthetic origin.

15. A composition according to claim 1, wherein said at least one oil is chosen from:
hydrocarbon-based oils of animal origin;
hydrocarbon-based plant oils; sunflower oil; corn oil; soybean oil; marrow oil; grapeseed oil; groundnut oil; sweet almond oil; beauty-leaf oil; palm oil; sesame oil; hazelnut oil; apricot oil; macadamia oil; castor oil; avocado oil; caprylic/capric acid triglycerides; jojoba oil; and karite butter;
linear and branched hydrocarbons of mineral and synthetic origin;
synthetic esters and ethers; hydroxylated esters; polyol esters; and pentaerythritol esters;
fatty alcohols comprising 12 to 26 carbon atoms;
fluoro oils chosen from partially hydrocarbon-based and silicone-containing oils;
silicone oils; alkyldimethicones; silicones modified with at least one group chosen from aliphatic and aromatic groups, which are optionally fluorinated, and functional groups; and phenylsilicone oils;
volatile silicone oils and cyclocopolymers; hydrocarbon-based volatile oils; and volatile fluoro oils.

16. A composition according to claim 15, wherein said hydrocarbon-based oils of animal origin are perhydrosqualene.

17. A composition according to claim 15, wherein said hydrocarbon-based plant oils are liquid triglycerides of fatty acids comprising 4 to 10 carbon atoms.

18. A composition according to claim 17, wherein said liquid triglycerides are chosen from heptanoic and octanoic acid triglycerides.

19. A composition according to claim 15, wherein said caprylic/capric acid triglycerides are those sold by the company Stearineries Dubois or those sold under the names Miglyol 810, 812 and 818 by the company Dynamit Nobel.

20. A composition according to claim 15, wherein said linear and branched hydrocarbons of mineral and synthetic origin are chosen from liquid paraffins and derivatives thereof, petroleum jelly, polydecenes, purcellin oil, and hydrogenated polyisobutene.

21. A composition according to claim 20, wherein said hydrogenated polyisobutene is parleam.

22. A composition according to claim 15, wherein said synthetic esters and ethers are chosen from synthetic esters of fatty acids and synthetic ethers of fatty acids.

23. A composition according to claim 22, wherein said synthetic esters of fatty acids and synthetic ethers of fatty acids are chosen from the oils of formula $R_3COOR_4$, wherein $R_3$ is a higher fatty acid residue comprising 7 to 29 carbon atoms, and $R_4$ is a hydrocarbon-based chain comprising 3 to 30 carbon atoms.

24. A composition according to claim 23, wherein said oils of formula $R_3COOR_4$ are chosen from purcellin oil, isopropyl myristate, 2-ethylhexyl palmitate, 2-octyldodecyl stearate, 2-octyldodecyl erucate, and isostearyl isostearate.

25. A composition according to claim 15, wherein said hydroxylated esters are chosen from isostearyl lactate, octyl hydroxystearate, octyldodecyl hydroxystearate, diisostearyl malate, triisocetyl citrate, fatty alkyl heptanoates, fatty alkyl octanoates and fatty alkyl decanoates.

26. A composition according to claim 15, wherein said polyol esters are chosen from propylene glycol dioctanoate, neopentyl glycol diheptanoate, and diethylene glycol diisononanoate.

27. A composition according to claim 15, wherein said fatty alcohols comprising 12 to 26 carbon atoms are chosen from octyldodecanol, 2-butyloctanol, 2-hexyldecanol, 2-undecylpentadecanol, and oleyl alcohol.

28. A composition according to claim 15, wherein said silicone oils are chosen from volatile and non-volatile, linear and cyclic polydimethylsiloxanes.

29. A composition according to claim 15, wherein said silicone oils are silicones modified with at least one group chosen from hydroxyl, thiol and amine groups.

30. A composition according to claim 15, wherein said phenylsilicone oils are chosen from polyphenylmethylsiloxanes and phenyltrimethicones.

31. A composition according to claim 15, wherein said volatile silicone oils are chosen from cyclic and linear volatile silicones.

32. A composition according to claim 15, wherein said hydrocarbon-based volatile oils are isoparaffins.

33. A composition according to claim 1, wherein said at least one oil is present in an amount ranging from 5% to 99% by weight relative to the total weight of the composition.

34. A composition according to claim 33, wherein said at least one oil is present in an amount ranging from 20% to 75% by weight relative to the total weight of the composition.

35. A composition according to claim 1, wherein said composition comprises less than 2% by weight of wax, relative to the total weight of the composition.

36. A composition according to claim 35, wherein said composition comprises less than 0.5% by weight of wax, relative to the total weight of the composition.

37. A composition according to claim 36, wherein said composition comprises 0% of wax.

38. A composition according to claim 1, wherein said composition further comprises at least one dyestuff.

39. A composition according to claim 38, wherein said at least one dyestuff is chosen from lipophilic dyes, hydrophilic dyes, pigments and nacres usually used in cosmetic and dermatological compositions.

40. A composition according to claim 38, wherein said at least one dyestuff is present in an amount ranging from 0.01% to 40% by weight relative to the total weight of the composition.

41. A composition according to claim 40, wherein said at least one dyestuff is present in an amount ranging from 5% to 25% by weight relative to the total weight of the composition.

42. A body hygiene composition, a hair composition, a make-up composition for facial or body skin or for mucous membranes, a care composition for the skin or mucous membranes, an antisun composition, or a self-tanning composition comprising at least one oil and at least one compound of formula I below:

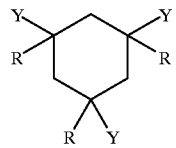

wherein:
the variables R are chosen, independently of each other, from a hydrogen atom and a linear or branched, saturated hydrocarbon-based chain comprising 1 to 6 carbon atoms;
the variables Y are chosen, independently of each other, from the groups —CO—S—R', —CO—NHR', NH—COR' and —S—COR', wherein the variables R' are chosen, independently of each other, from:
a hydrogen atom,
an aryl group,
an aralkyl group, and
a linear, branched, or cyclic, saturated hydrocarbon-based chain comprising 1 to 22 carbon atoms, which is optionally substituted with one or more groups chosen from aryl, ester, amide and urethane groups, and/or optionally comprises one or more hetero atoms chosen from O, S and N, and/or is optionally substituted with one or more fluorine atoms and/or one or more hydroxyl radicals;
wherein said composition is in solid form, and wherein said composition comprises less than about 5% by weight of wax relative to the total weight of the composition.

43. A composition according to claim 42, wherein said body hygiene composition is in the form of deodorant sticks.

44. A composition according to claim 42, wherein said hair composition is in the form of styling sticks or make-up sticks for the hair.

45. A composition according to claim 42, wherein said make-up composition is in the form of lipsticks, foundations cast as a stick or a dish, face powders, eyeshadows, fixing bases to be applied to a conventional lipstick, concealer sticks, lip glosses, eyeliners, mascaras, or temporary tattoo products.

46. A composition according to claim 42, wherein said care composition is in the form of a lipcare balm or base, a body ointment, or a daily care cream.

47. A composition according to claim 1, wherein said composition is in translucent or transparent form.

48. A composition according to claim 47, wherein said composition is in the form of a translucent or transparent anhydrous stick.

49. A composition according to claim 1, wherein said composition has a maximum light transmittance value, irrespective of the wavelength from 400 nm to 800 nm, of at least 2%, through a 1 cm-thick sample.

50. A composition according to claim 1, wherein said composition has a hardness ranging from 0.04 N to 3 N.

51. A composition according to claim 50, wherein said composition has a hardness ranging from 0.1 N to 2.5 N.

52. A composition according to claim 51, wherein said composition has a hardness ranging from 0.5 N to 2 N.

53. An optionally colored transfer-resistant or non-migrating composition comprising at least one oil and at least one compound of formula I below:

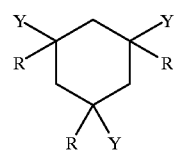

wherein:
the variables R are chosen, independently of each other, from a hydrogen atom and a linear or branched, saturated hydrocarbon-based chain comprising 1 to 6 carbon atoms;
the variables Y are chosen, independently of each other, from the groups —CO—S—R', —CO—NHR', NH—COR' and —S—COR', wherein the variables R' are chosen, independently of each other, from:
a hydrogen atom,
an aryl group,
an aralkyl group, and
a linear, branched, or cyclic, saturated hydrocarbon-based chain comprising 1 to 22 carbon atoms, which is optionally substituted with one or more groups chosen from aryl, ester, amide and urethane groups, and/or optionally comprises one or more hetero atoms chosen from O, S and N, and/or is optionally substituted with one or more fluorine atoms and/or one or more hydroxyl radicals;

wherein said composition is in solid form, and wherein said composition comprises less than about 5% by weight of wax relative to the total weight of the composition.

54. A composition according to claim 1, wherein said at least one compound of formula I is present in an amount effective to structure and/or gel said composition.

55. A cosmetic treatment process for a support chosen from facial and body skin, mucous membranes and keratin fibers, comprising applying to said support a composition comprising at least one oil and at least one compound of formula I below:

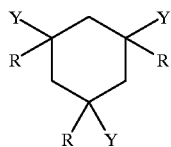

wherein:
the variables R are chosen, independently of each other, from a hydrogen atom and a linear or branched, saturated hydrocarbon-based chain comprising 1 to 6 carbon atoms;
the variables Y are chosen, independently of each other, from the groups —CO—S—R', —CO—NHR', NH—COR' and —S—COR', wherein the variables R' are chosen, independently of each other, from:
a hydrogen atom,
an aryl group,
an aralkyl group, and
a linear, branched, or cyclic, saturated hydrocarbon-based chain comprising 1 to 22 carbon atoms, and which is optionally substituted with one or more groups chosen from aryl, ester, amide and urethane groups, and/or optionally comprises one or more hetero atoms chosen from O, S and N, and/or is optionally substituted with one or more fluorine atoms and/or one or more hydroxyl radicals;

wherein said composition is in solid form, and wherein said composition comprises less than about 5% by weight of wax relative to the total weight of the composition.

56. A process according to claim 55, wherein said composition is a cosmetic or dermatological composition.

57. A process according to claim 55, wherein said variables R are chosen, independently of each other, from a hydrogen atom and a linear or branched, saturated hydrocarbon-based chain comprising 1 to 4 carbon atoms.

58. A process according to claim 55, wherein said aralkyl group is an aryl group substituted with a linear or branched, saturated hydrocarbon-based chain comprising 1 to 22 carbon atoms.

59. A process according to claim 58, wherein said aralkyl group is an aryl group substituted with a linear or branched, saturated hydrocarbon-based chain comprising 10 to 18 carbon atoms.

60. A process according to claim 55, wherein said variables R' are chosen, independently of each other, from:
a hydrogen atom,
an aryl group,
an aralkyl group, and
a linear, branched, or cyclic, saturated hydrocarbon-based chain comprising 10 to 18 carbon atoms, which is optionally substituted with one or more groups chosen from aryl, ester, amide and urethane groups, and/or optionally comprises one or more hetero atoms chosen from O, S and N, and/or is optionally substituted with one or more fluorine atoms and/or one or more hydroxyl radicals.

* * * * *